US005650277A

United States Patent [19]
Navot et al.

[11] Patent Number: 5,650,277
[45] Date of Patent: Jul. 22, 1997

[54] METHOD OF DETERMINING THE PRESENCE AND QUANTIFYING THE NUMBER OF DI- AND TRINUCLEOTIDE REPEATS

[75] Inventors: Nir Navot, Rosh Haayin; Nurit Eyal, Rehovot, both of Israel

[73] Assignee: Diagenetics Ltd., Rehovot, Israel

[21] Appl. No.: 317,431

[22] Filed: Oct. 4, 1994

Related U.S. Application Data

[63] Continuation-in-part of Ser. No. 84,505, Jul. 1, 1993, abandoned, which is a continuation of Ser. No. 919,872, Jul. 27, 1992, abandoned.

[30] Foreign Application Priority Data

Jul. 2, 1992 [IL] Israel ........................................ 102382

[51] Int. Cl.⁶ .......................... C07H 21/04; C12P 19/34; C12Q 1/68
[52] U.S. Cl. ........................ 435/6; 435/91.1; 435/91.2; 435/91.52; 536/24.33; 935/77; 935/78
[58] Field of Search .................... 435/6, 91.1, 91.2, 435/91.52; 536/24-33; 935/77, 78

[56] References Cited

U.S. PATENT DOCUMENTS

| | | | |
|---|---|---|---|
| 5,075,217 | 12/1991 | Weber | 435/6 |
| 5,369,004 | 11/1994 | Polymeropoulos et al. | 435/6 |
| 5,378,602 | 1/1995 | Polymeropoulos et al. | 435/6 |
| 5,468,610 | 11/1995 | Polymeropoulos et al. | 435/6 |

OTHER PUBLICATIONS

Yamamoto et al., Bioch. Biophys. Res. Comm. 182(2):507–513 Jan. 31, 1992.
Jalanko et al., Clin. Chem. 38(1):39–43 1991.
Sokolov, Nuc. Acids Res. 18(12):3671 Jun. 25, 1990.
Kuppuswamy et al., Proc. Natl. Acad. Sci., USA, 88:1143–1147 1991.
Singer–Sam et al., PCR Methods and Applications 1:160–163 1992.

*Primary Examiner*—W. Gary Jones
*Assistant Examiner*—Paul B. Tran
*Attorney, Agent, or Firm*—Mark M. Friedman

[57] ABSTRACT

A method aimed at the quantification of di- and trinucleotide repeat which includes (a) treating a sample containing the nucleic acids of interest to obtain unpaired nucleotide bases spanning the position of the repeats and flanking regions, if the nucleic acids are not already single stranded; (b) contacting the unpaired nucleotide bases with an oligonucleotide primer capable of hybridizing with a stretch of nucleotide bases present in the nucleic acid of interest preferably 3' of the trinucleotide repeats to be quantified, so as to form a duplex between the primer and the nucleic acid of interest; (c) providing means to ensure that the examined nucleic acid and the oligonucleotide primer are confined to a reaction chamber at all further steps; (d) contacting the duplex with a primer extension unit which is capable of base pairing with the first nucleotide base in the core sequence of the repeats, and a template dependent extension enzyme; (e) eliminating non-incorporated primer extension units; (f) contacting the template primer duplex with a primer extension unit which is capable of base pairing with the second nucleotide base in the core sequence of the repeats, and a template dependent extension enzyme; (g) eliminating non-incorporated primer extension units; (h) contacting the template primer hybrid with a primer extension unit which is capable of base pairing with the third nucleotide base in the core sequence of the repeats; a detection moiety containing, primer extension unit which is capable of base pairing with a nucleotide base 5' of the repeats region, said nucleotide base being the first nucleotide base of a type not included among the nucleotide bases in the core sequence of the trinucleotide repeats; and a template dependent extension enzyme; (i) eliminating non-incorporated primer extension units; (j) detecting for the presence of detection moiety containing primer extension unit; (k) steps (d) to (j) are repeated until detecting said detection moiety; (l) the number of repeats as stated under (k) enables the determination of the number of trinucleotide repeats, therefore enabling determination of the exact repetition number.

45 Claims, 4 Drawing Sheets

METHOD OF DETERMINING THE PRESENCE AND QUANTIFYING THE NUMBER OF DI- AND TRINUCLEOTIDE REPEATS

This is a continuation in part of U.S. patent application Ser. No. 08/084,505 filed Jul. 1st, 1993, now abandoned which is a continuation in part of U.S. patent application Ser. No. 07/919,872 filed Jul. 27th, 1992, now abandoned.

FIELD AND BACKGROUND OF THE INVENTION

The present invention relates to the determination of di- and trinucleotide repeat mutations involved with increasing number of genetically inherited diseases characterized by the expansion or the amplification of a core di- or trinucleotide sequences.

More particularly, the present invention concerns a sensitive method, an automated instrument and kits for unequivocally quantifying the exact number of di- and trinucleotide repeats in preselected genetic loci.

The present method, instrument and kits are also useful for determining the number of head to tail repeat sequences of two or more nucleotide bases, provided that the core sequence consists of no more than three types of nucleotide bases such as, for example, adenine (A), guanine (G) and cytosine (C) in a core sequence composed of $(AAGCGCA)_n (n \geq 1)$.

In recent years, increasing number of genetically inherited diseases were found to be associated with mutations designated unstable trinucleotide repeat mutations in which a core sequence of three nucleotide bases is expanded or amplified, such that affected individuals and in some cases carriers, contain more repeats than apparently healthy ones, in the particular DNA locus implicated with the disease.

More recently, a new cancer gene was discovered and was shown to cause segments of DNA to be abnormally repeated in pairs and/or triplets in tumor cells of individuals carrying the cancer gene. In this case hundred of thousands of short units of DNA are copied over and over again, presumably destroying the tumor cells ability to control their growth. This phenomenon is somewhat different than the expansion of unstable trinucleotide repeats in hereditary diseases since it occurs in many DNA loci within the same cell. Nevertheless, there is a good reason to believe that both phenomena are propagated by similar mechanisms. See, Kolata G. Health/Science section, The National Herald Tribune, Thursday, May 13, 1993.

So far, seven genetically transmitted diseases, each involving a unique genetic locus, have been implicated with trinucleotide repeat mutations. These include: Fragile XA (A site, Martin Bell) syndrome (FRAXA); spinal and bulbar muscular atrophy, SBMA (Kennedy disease); Myotonic dystrophy (Curschmann Steinert, DM); Huntington's disease (HD); Spinocerebellar ataxia type 1 (SCA1); Fragile XE (E site) mental retardation (FRAXE MR); and Dentatorubral pallidoluysian atrophy (DRPLA). Since di- and trinucleotide repeats have been observed within or close to a number of additional human genes by gene-bank searches, it is conceivable that di- and trinucleotide amplifications may be involved in the causation of other genetic diseases as well.

Fragile XA syndrome is an X chromosome linked recessive disorder with incomplete penetrance. It is characterized by moderate to severe mental retardation and other phenotype characteristics, and is one of the most common forms of mental retardation with an estimated incidence of 1 in 1250 males and corresponding 1 in 2500 females (heterozygotes), rendering this disease one of the most common human diseases and the most common form of familial retardation. Fragile X chromosomes present their unique phenotype when leukocyte cells carrying them are grown in culture under folate starvation. As mentioned, the fragile X syndrome is characterized by incomplete penetrance hence (1) some males, referred to as normal transmitting males (NTMs), are clinically normal but are inferred to carry the genetic defect by a position in pedigrees rendering them obligatory carriers; (2) one third of female carriers have evidence of mild mental impairment. Genetic linkage studies effected by restriction fragment length polymorphism analysis of informative pedigrees; and somatic cell hybrid studies of hamster chromosomes carrying translocated segments of human fragile X chromosomes in cells grown in culture under folate starvation, enabled the localization of the fragile X gene to chromosomal band q27.3 on the X chromosome (Xq27.3). Eventually the fragile X defective gene, designated fragile X mental retardation 1 (FMR1), was isolated via positional cloning and led to the discovery of a highly polymorphic $(CGG)_n$ sequence within its 5' untranslated region. Population and fragile X patients screening revealed that healthy individuals are characterized by low numbers of the $(CGG)_n$ trinucleotide repeat (n=6–52); carriers are characterized by medium numbers of the $(CGG)_n$ trinucleotide repeat (n=50–200); and affected individuals are characterized by high numbers of the $(CGG)_n$ trinucleotide repeat (n=230–1000). When the $(CGG)_n$ trinucleotide repeats of the FMR1 gene exceeds approximately 230 repeats, the DNA of the entire 5' region of the gene becomes abnormally methylated. This methylation extends upstream into and beyond the promoter region and results in the transcriptional suppression of the FMR1 gene leading to the cessation of the FMR1 protein production which is probably the cause of the phenotype. See Annemieke J. M. H. (1991) Cell, 65:905–914; Pieretti M. (1991) Cell, 66:817–822; Caskey T. C. et al. (1992) Science, 256:784–788.

Spinal and bulbar muscular atrophy (SBMA), like the fragile X syndrome, is a rare X linked recessive genetic disorder characterized by adulthood onset of progressive muscular weakness of upper and lower extremities which is secondary to neural degeneration. Affected males have reduced fertility and excessive development of the male mammary glands (gynecomastia); female carriers have few or no symptoms. Genetic linkage analysis of informative pedigrees enabled the localization of SBMA to chromosome Xq11–12, the region where the gene encoding the androgen receptor (AR) was previously localized, rendering this gene a candidate for SBMA. Studies of the AR gene revealed a highly polymorphic $(CAG)_n$ trinucleotide repeat, situated in exon 1, encoding a variable polyglutamine stretch in the AR protein. Further studies of the AR gene from normal and SBMA affected individuals revealed that while low numbers of the $(CAG)_n$ trinucleotide repeat (n=12–34) characterize apparently healthy individuals, high numbers of the $(CAG)_n$ trinucleotide repeat (n=40–62) characterize SBMA affected individuals, while a carrier state is not yet known for this mutation. The influence of the expanded polyglutamine tract on the AR protein is not yet established, nevertheless, gain of function, leading to the SMBA phenotype is suspected. See, Albert R. et al. (1991) Nature, 352:77–79; Caskey T. C. et al. (1992) Science, 256:784–788.

Myotonic dystrophy (DM) is an autosomal dominant disease characterized by myotonia, cardiac arrhythmias, cataracts, male balding, male infertility (hypogonadism), and other associated endocrinopathies. The rare congenital form of DM is associated with profound newborn hypotonia and mental retardation. DM has a prevalence of 2.5–5.5 affected per 100,000 individuals. DM was mapped by genetic linkage to chromosome 19q13.3 and the DM gene, designated myotonin protein kinase (MT-PK), was isolated via positional cloning and other molecular methods. Further studies revealed a polymorphic $(GCT)_n$ trinucleotide repeat situated in the 3' untranslated region of the MT-PK gene. Analyses of the MT-PK gene from normal and DM affected individuals revealed that while low numbers of the $(GCT)_n$ trinucleotide repeat (n=5–37) characterize apparently healthy individuals, high numbers of the $(GCT)_n$ trinucleotide repeat (n=100->1000) characterize DM affected individuals, while the carrier state is characterized by medium numbers of the $(GCT)_n$ trinucleotide repeat (n≅50–100). Further studies have revealed that expansion of the $(GCT)_n$ trinucleotide repeat leads to increased MT-PKmRNA stability, therefore to the production of more MT-PK protein suspectedly leading, directly or indirectly, to the DM phenotype. See, Fu Y. H. et al. (1992) Science, 255:1256–1258; Caskey T. C. et al. (1992) Science, 256:784–788.

Huntington's disease (HD) is a devastating late onset autosomal dominant neurodegenerative disorder characterized by progressive neurodegeneration with personality disturbance, involuntary movements, cognitive loss and an inexorable progression to death 15–20 years from time of onset. HD occurs with a frequency of 1 in 10,000 individuals in most populations of Caucasian descent. The HD gene was localized to chromosome 4p16.3 by genetic linkage analysis with polymorphic DNA markers. Recently, following 10 years of extensive research, the defective gene causing HD, designated IT15, was isolated and a polymorphic $(CAG)_n$ trinucleotide repeat encoding a polyglutamine stretch, situated in exon 1 of the gene was discovered. It was further found that the $(CAG)_n$ trinucleotide repeat is expanded in HD chromosomes (n=42–100) as compared with normal chromosomes (n=11–36), presumably leading to IT15 proteins gain of function, suspectedly leading to the HD phenotype. See, The Huntington's disease collaborative research group (1993) Cell, 72:971–983; Zuhlke C. et al. (1993) Hum. Molec. Genet. 2:1467–1469.

Spinocerebellar ataxia type 1 (SCA1) is a progressive late onset autosomal dominant disorder characterized by ataxia, ophthalmoparesis and variable degree of motor weakness due to neurodegeneration of the cerebellum, spinal chord and brain stem, leading to complete disability and death 10–20 years after onset. The SCA1 gene was localized to chromosome 6p22–p23 due to strong genetic linkage with the highly polymorphic HLA locus and other polymorphic DNA markers. The defective gene causing SCA1, was isolated in a yeast artificial chromosome contig and subcloned into cosmids. A polymorphic $(CAG)_n$ trinucleotide repeat encoding a polyglutamine stretch, situated in exon 1 of the SCA1 gene was discovered. It was further found that the $(CAG)_n$ trinucleotide repeat is expanded in SCA1 chromosomes (n=43–81) as compared with normal chromosomes (n=19–36), presumably leading to SCA1 proteins gain of function, suspectedly leading to the SCA1 phenotype. See, Orr H. T. et al. (1993) Nature Genetics, 4:221–226.

Fragile XE mental retardation (FRAXE MR), like FRAXA is an X chromosome linked recessive disorder with incomplete penetrance. It is characterized by moderate to severe mental retardation and other phenotype characteristics. Like FRAXA, FRAXE chromosomes present their unique phenotype when leukocyte cells carrying them are grown in culture under folate starvation. Genetic linkage studies enabled the localization of the FRAXE gene to chromosome Xq28. Eventually the FRAXE gene was isolated via positional cloning and led to the discovery of a highly polymorphic $(GCC)_n$ trinucleotide repeat segregating with the disease. Population and FRAXE patients screening revealed that healthy individuals are characterized by low numbers of the $(GCC)_n$ trinucleotide repeat (n=6–25); carriers are characterized by medium numbers of the $(GCC)_n$ trinucleotide repeat (n=116–133); and affected individuals are characterized by high numbers of the $(CGG)_n$ trinucleotide repeat (n=200–850). When the $(CGG)_n$ trinucleotide repeat of the FRAXE gene exceeds approximately 200 repeats, the DNA of a CpG island located in the trinucleotide repeats vicinity becomes abnormally methylated, presumably leading to the secession of the FRAXE protein production, which is probably the cause of the phenotype. See Knight S. J. L. et al. (1993) Cell, 74:127–134.

Dentatorubral pallidoluysian atrophy (DRPLA) is a late onset autosomal dominant neurodegenerative disorder, prevalent in Japan, characterized by a varying combinations of progressive myoclonus, epilepsy, ataxia, choreoathetosis and dementia. Neuropathological changes consist of combined degeneration of the dentatorubal and pallidoluysian systems of the central nervous system. The disease is further characterized by variable penetrance, even in a single family. Linkage analysis in DRPLA families enabled to localize the DRPLA gene to chromosome 12p12–13. The DRPLA gene was isolated via screening for $(CAG)_n$ unstable trinucleotide repeat that was found to be located in exon 1 of the gene, encoding a variable polyglutamine stretch in the DRPLA protein. It was further found that the $(CAG)_n$ trinucleotide repeat is expanded in DRPLA chromosomes (n=49–75) as compared with normal chromosomes (n=7–23), presumably leading to DRPLA proteins gain of function, suspectedly leading to the DRPLA phenotype. See, Nagafuchi S. et al. (1994) Nature Genetics, 6:14–18; Koide R. et al. (1994) Nature Genetics, 6:9–13.

Because of the high frequency, variable penetrance and instability of Fragile XA syndrome and other genetically inherited disorders associated with trinucleotide repeats expansion, there is a widely recognized need for, and it would be highly advantageous to have, a low cost method, demanding merely non skilled personnel for its execution, that enables the efficient and accurate determination of the number of repeats in various genes.

Unlike the common gene mutations (e.g., Cystic Fibrosis ΔF508), which are stable, that is, they are transmitted unchanged along the generations of pedigrees, the situation is somewhat different for the trinucleotide repeat mutations which are characterized by instability, that is, when the number of repeats exceeds a threshold value, these mutations have a tendency to expand and include a greater number of repeats (1) when vertically transmitted from parents to children along genetic traits; and (2) when somatically transmitted to daughter cells in a given individual, a phenomena designated somatic instability, yielding mosaicism.

The two types of instability characterizing trinucleotide repeat mutations will be exemplified herein for the fragile XA syndrome.

Fragile XA unstable alleles are observed in normal transmitting males (NTMs) their asymptomatic daughters and symptomatic male grandchilds. When the number of trinucleotide repeats of such alleles was determined, it was found to increase along generations, in one example from 82 in the NTM father to 83 in the asymptomatic daughter (90 in a second asymptomatic daughter) to >200 in the diseased grandchildren. The 82, 83 and 90 repeats containing alleles are referred to as premutation alleles. It was a study of numerous families of this type that permitted a correlation of the phenomenon of anticipation (earlier ages of onset or severeness in successive generations) and the molecular events of the $(CGG)_n$ expansion. NTMs carry numbers of CGG repeats outside the range of normal and bellow those found in affected males. Such males transmit the repeats to their progeny with relatively small changes in the repeats number. On the other hand females who carry similar premutation alleles are prone to bear progeny (male or female) with large expansion of the repeats region. Thus, large CGG amplification associated with fragile XA syndrome appears to be predominantly a female meiotic event. See, Caskey T. C. et al. (1992) Science, 256:784–788.

Many fragile XA diseased individuals were found to be mosaic in respect with the number of the CGG trinucleotide repeats characterizing different cells in their body, a phenomenon indicating somatic instability of expanded repeats.

Instability, characterized by expansion of trinucleotide repeats, is observed also in DM, HD, FRAXE, DRPLA and SCA1 pedigrees. As opposed to FRAXA, DM and FRAXE high risk alleles can expand to similar extent via both male and female meiosis and to the best of our knowledge somatic mosaicism was not yet observed in DM and FRAXE patients. High risk alleles were not yet found for HD and DRPLA, that is, alleles of these diseases are either carrying or not carrying the disease. Nevertheless, HD repeats are also unstable in more than 80% of meiotic transmissions but, on the other hand, they are characterized by increasing, or alternatively, decreasing numbers of repeats with the largest increase occurring in paternal transmission (Duyao M. et al. (1993) Nature Genetics, 4:387–392), whereas DRPLA alleles have a tendency to increase in size along generations. See, Nagafuchi S. et al. (1994) Nature Genetics, 6:14–18; Koide R. et al. (1994) Nature Genetics, 6:9–13.

Attempts to correlate the size of trinucleotide repeat mutations and the severity of the associated genetic diseases were made for fragile XA syndrome, myotonic dystrophy, dentatorubral pallidoluysian atrophy and spinocerebellar ataxia type 1.

For fragile XA, as expected, median IQ score was significantly lower for females carrying a fully expanded mutation (above 230 repeats) than for females carrying a premutation (50–200 repeats) on one of their X chromosomes. On the other hand, no significant relationship was found between IQ score and number of CGG repeats, see, Taylor A. K. et al. (1994) JAMA, 271:507–514. Nevertheless, it was found that prenatal DNA studies of the number of CTG trinucleotide repeats characterizing myotonic dystrophy alleles can improve the estimation of clinical severity; and that the number of CAG trinucleotide repeats in spinocerebellar ataxia type 1 and dentatorubral pallidoluysian atrophy is correlated with increased progression of the disease (Nagafuchi S. et al. (1994) Nature Genetics, 6:14–18; Koide R. et al. (1994) Nature Genetics, 6:9–13; Orr H. T. et al. (1993) Nature Genetics, 4:221–226).

Attempts to correlate between the size of trinucleotide repeat mutations and the age of onset of Huntington's disease resulted in finding a reversed correlation confined to the upper range of trinucleotide repeat numbers (ca. 60–100 repeats), see, Andrew S. E. et al. (1993) Nature Genetics, 4:398–403. Furthermore, for spinocerebellar ataxia type 1 and dentatorubral pallidoluysian atrophy (Nagafuchi S. et al. (1994) Nature Genetics, 6:14–18; Koide R. et al. (1994) Nature Genetics, 6:9–13), a direct correlation between the number of the $(CAG)_n$ trinucleotide repeats expansion and earlier ages of onset was found.

Collectively, these data call for the development of a reliable, accurate and easy to operate di- and trinucleotide repeats quantification method aimed at post and prenatal diagnosis and prognosis.

Three basic methods are currently used to determine the number of di- and trinucleotide repeats in any particular locus, these are: (1) "Southern" blot analysis; (2) in vitro amplification via the Polymerase Chain Reaction (PCR) and PCR fragment size determination; (3) DNA sequencing (usually of PCR amplified fragments).

"Southern" blot analysis for the quantification of di- and trinucleotide repeats is a method based upon: (1) enzymatic cleavage of genomic DNA obtained from the examined individual via sequence specific restriction enzymes cleaving the DNA at many sites including the flanking regions both 5' and 3' to the DNA region containing the examined di- or trinucleotide repeats; (2) gel electrophoresis aimed at size separation of the DNA fragments obtained under step (1); (3) blotting or transferring the cleaved and size separated DNA fragments to a test surface; (4) preparing a labeled probe capable of specific hybridization with the blotted DNA fragment containing the repeats; (5) hybridizing the labeled probe with the blotted DNA fragments; (6) washing off probe excess to obtain specific hybridization and to reduce non-specific and background signals; (7) detecting positive signals via means dependent upon the probe labeling technique employed under step (4); (8) interpreting the results by determining the size of the fragment hybridized to the labeled probe; and finally (9) calculating the number of di- or trinucleotide repeats.

"Southern" blot analysis for the quantification of di- and trinucleotide repeats has major drawbacks: (1) the method is primarily dependent upon the existence of suitable restriction enzymes recognition sites in the immediate 5' and 3' flanking region of the repeats region; (2) gel electrophoresis employed under "Southern" blot analysis has low resolution capacity for small size variations, therefore this method is not suitable for monitoring small variations in the number of the di- or trinucleotide repeats; (3) "Southern" blot analysis is not capable of distinguishing between size variations due to di- or trinucleotide repeats expansion/de-expansion or other molecular events such as the loss or the formation of a restriction enzyme recognition site/s due to point mutation, deletions or insertions, yielding a di- or trinucleotide repeats expansion/de-expansion independent length polymorphism; (4) "Southern" blot analysis demands accurate execution of a multistep procedure, of which most steps include several complicated steps, are time consuming and require highly skilled personnel for their routine execution, especially gel electrophoresis, blotting and hybridization; (5) highly skilled personnel are also needed for interpreting the results and for calculating the di- or trinucleotide repeats number; (6) gel electrophoresis, hybridization and washing conditions may vary considerably depending upon fragment size and sequence, therefore, "Southern" blot analysis requires different calibration of the procedure for any given disease; and last but not least (7) due to its being a multistep procedure, "Southern" blot analysis is not easily applicable for complete automatization.

In vitro amplification via the Polymerase Chain Reaction (PCR) and PCR fragment size determination is easier for execution as compared with "Southern" blot analysis and involves less steps, these are: (1) PCR amplification of the di- or trinucleotide repeats region using PCR primers from the 5' and 3' flanking regions of the repeats; (2) size determination of thus obtained PCR fragments via high resolution gel electrophoresis; and (3) calculating the number of the di- or trinucleotide repeats. See, Erster S. H. (1992) Hum. Genet., 90:55–61.

Although this approach is simpler and therefore easier for routine execution it shares some of the drawbacks described for "Southern" blot analysis, these include: (1) the PCR approach is not capable of distinguishing between size variations due to di- or trinucleotide repeats expansion/de-expansion or other molecular events such as the loss or gain of sequences due to deletions or insertions in the 5' and/or 3' repeats flanking regions, yielding a di- or trinucleotide repeats expansion/de-expansion independent PCR fragment length polymorphism; (2) a high resolution gel electrophoresis is required for resolving small size variations in the PCR fragments, this calls for highly skilled personnel and therefore not suitable as a routine diagnostics procedure; (3) highly skilled personnel are also needed for interpreting the results and for calculating the number of the di- or trinucleotide repeats. In addition: (4) the PCR approach is not suitable for quantifying highly expanded di- or trinucleotide repeats, since its amplifying capacity is limited to relatively small fragments, therefore, in cases where the fragment to be amplified exceeds a certain size limit the PCR reaction will fail to yield a specific product; and (5) some of the di- or trinucleotide repeats form highly GC rich stretches of DNA which are not easily amplified via standard PCR protocols.

The most basic method for determination of di- or trinucleotide repeats number is DNA sequencing. The most widely used sequencing method is based on the dideoxynucleotide chain termination procedure. The technique involves the incorporation of dideoxynucleotides with the aid of a DNA extension enzyme at the 3'-end of an elongating DNA chain. Once the dideoxynucleotide has been incorporated, further elongation of the chain is blocked. See, Sanger F. (1981), Science 214, 1205 1210. Recently automated DNA sequencing techniques have been developed which provide for more rapid and safer DNA sequencing. One such approach utilizes a set of four chain terminating fluorescently labeled dideoxynucleotides. See Chehab, F. F., et al. (1989), Proc. Natl. Acad. Sci. (USA) 86, 9178 9182; Prober, J. M., et al. (1987), Science 238, 336 341; Smith, L. M., et al. (1980), Nature 321, 674 678). In this method succinyl fluorescein dyes are used. Each dideoxynucleotide receives a different dye of different absorption and emission characteristics. Thus, DNA molecules labeled with each of the different dideoxynucleotides may be distinguished from one another. Using these dideoxynucleotides, it is possible to sequence a DNA segment by carrying out a single reaction in which all four of the differently labeled dideoxynucleotides are added together into a single reaction mixture and the resulting labeled oligonucleotide fragments may then be resolved by polyacrylamide gel electrophoresis in a single sequencing lane on the gel. The gel is then scanned by a fluorimeter capable of distinguishing the different fluorescent labels. The sequence of the different labels along the lane is then translated into the sequence of the tested DNA segment.

DNA sequencing as a method for quantification of di- or trinucleotide repeat numbers has few major drawbacks, these are: (1) a high voltage and high resolution gel electrophoresis is required for resolving the single stranded DNA nested fragments obtained during the sequencing reaction, differing from each other merely by one nucleotide base, this calls for highly skilled personnel and therefore not suitable as a routine diagnostics procedure; (2) some of the di- or trinucleotide repeats form highly GC rich stretches of DNA which are not easily sequenced via standard sequencing protocols; and (3) the sequencing approach is not suitable for quantifying large di- or trinucleotide repeats since it is limited by the resolution power of the sequencing gel.

It is an object of the present invention to provide a simple, reliable, rapid, highly accurate and easy to operate di- and trinucleotide repeats quantification method aimed at post and prenatal diagnosis and prognosis which do not require electrophoresis or similar separation according to size as part of its methodology.

It is another object of the present invention to provide a diagnostic kit and an automated instrument to be used for carrying out the above method of the invention.

SUMMARY OF THE INVENTION

According to the present invention, there is provided a method, named Trinucleotide Repeats Quantification (TriQ), for determining the number of di- and trinucleotide repeats associated with various diseases.

The method of the invention depends upon counting successive steps of incorporation of two to three types of primer extension units, depending on the core repeat sequence, to a 3'-end of an oligonucleotide primer annealed to a single stranded nucleic acid sequence template preferably 3' of the di- or trinucleotide repeats region, said counting being terminated at the incorporation of an additional type of primer extension unit, containing a detection moiety, capable of base pairing with a nucleotide base located 5' of the repeats region, said nucleotide base is the first nucleotide base that is not identical with the nucleotide bases in the core sequence of the repeats in said nucleic acid template.

One of the applications of the current invention is to enable quick determination of the number of di- or trinucleotide repeats in genetic loci containing such repeats.

In the broad application of the method of the invention the addition of primer extension units to a 3'-end of the oligonucleotide primer is carried out singularly, that is, primer extension units complementary to the di- or trinucleotide repeats core sequence are added at the 3'-end of the elongating oligonucleotide primer one after the other. Also according to the broad application of the method of the invention the detection moiety containing primer extension unit that is complementary to a nucleotide base located 5' of the repeats region, which is the first nucleotide base not identical with the nucleotide bases in the core sequence of the repeats, is present in all incorporation steps.

In a preferred use of this application of the present invention for the determination of the number of trinucleotide repeats in genetic loci containing such repeats, the addition of primer extension units to a 3'-end of the oligonucleotide primer is carried out in pairs followed by a single primer extension unit addition, or alternatively, vice versa, a single primer extension unit addition is followed by the addition of a pair.

Also according to the preferred use of this application of the method of the invention a detection moiety containing, primer extension unit that is complementary to a nucleotide base located 5' of the repeats region, said nucleotide base is the first nucleotide base not identical with the nucleotide bases in the core sequence of the repeats, is present only in some or all steps preceding the incorporation of a primer extension unit complementary to the first nucleotide base in the core sequence of the di- or trinucleotide repeats.

Another use of this application of the current invention enables genotyping of an individual, that is, to determine the genotype of an individual at any DNA locus containing di- or trinucleotide repeats, that is to quantify the number of repeats contained in any of said locus allele.

Yet another use of this application of the current invention enables the determination of the number of head to tail repeat sequences comprised of two or more core nucleotide bases, provided that the core repeat sequence consists of no more than three types of nucleotide bases.

According to features of preferred embodiments of the invention described below suitable detection moieties of primer extension units include those facilitating direct or indirect detection and which are permanently conjugated to any location at the primer extension unit, or alternatively, removable or destructible. Detecting the detection moiety, whether directly or indirectly, may be carrier out in the reaction chamber or in a different chamber depending whether the detection moiety is removable or not.

According to still further features in the described preferred embodiments, the extension moiety is a deoxyribonucleotide, such as dATP, dCTP, dGTP, dTTP and dUTP.

The oligonucleotide primer may be of any suitable length. Time and expense considerations tend to shift preference toward shorter oligonucleotide which is still sufficiently long to ensure high sequence specificity while at the same time ensuring rapid, easy and accurate preparation.

The sample of genetic material being tested by the method of invention may be in the form of RNA or DNA.

The extension moiety may, for example, be attached to any suitable detection moiety, such as a radioactive label, e.g., $^{32}P$ and various fluorescent labels. Another example involves nucleotides having a detection moiety attachment which may function for indirect detection.

According to further features of preferred embodiments described below reagents are collected and are reused in further steps.

Also according to the present invention, there is provided a diagnostic kit for quantifying the number of di- or trinucleotide repeats, consisting: (a) any number of suitable oligonucleotide primers (b) two or three primer extension units; (c) further one or two primer extension units of a type not included under (b), said primer extension units containing a detection moiety; (d) a template dependent extension enzyme; and (e) at least one buffer.

Also according to the present invention, there is provided an automated instrument suitable for executing the steps consisting the method of the invention.

BRIEF DESCRIPTION OF THE DRAWINGS

The invention is herein described, by way of example only, with reference to the accompanying drawings, wherein.

DESCRIPTION OF THE PREFERRED EMBODIMENTS

The present invention is of a novel method for determining the number of di- or trinucleotide repeats associated with various diseases.

The principles and operation of a method according to the present invention may be better understood with reference to the drawings and the accompanying description.

The present invention will be described in more detail with emphasis on a method for quantification of the number of trinucleotide repeats in genes, which repeats are associated with genetic disorders. While this application of the method of the invention is presently preferred, this is by no means the only application of the invention as will no doubt be appreciated by those skilled in the art. For example, the method has various other applications including, but not limited to, the detection of specific genetic sequences in samples such as nucleotide repeats characterized by a core sequence consisted of two or three types of nucleotides; those associated with certain genetic or other diseases and pathogenic microorganisms, for example bacteria and viruses; in testing of paternity; and in forensic medicine; cancers; and plant polymorphism.

As for quantifying the number of trinucleotide repeats in genes associated with trinucleotide repeats expansion the method of the invention depends upon counting successive steps of incorporation of two to three types of primer extension units, depending on the core repeat sequence, to a 3'-end of an oligonucleotide primer annealed to a single stranded nucleic acid sequence template preferably 3' of the trinucleotide repeats region, said counting being terminated at the incorporation of an additional type of primer extension unit, containing a detection moiety, capable of base pairing with the first nucleotide base of a type that is not included among the nucleotide bases in the core sequence of the repeat in said nucleic acid template.

Figure 1:
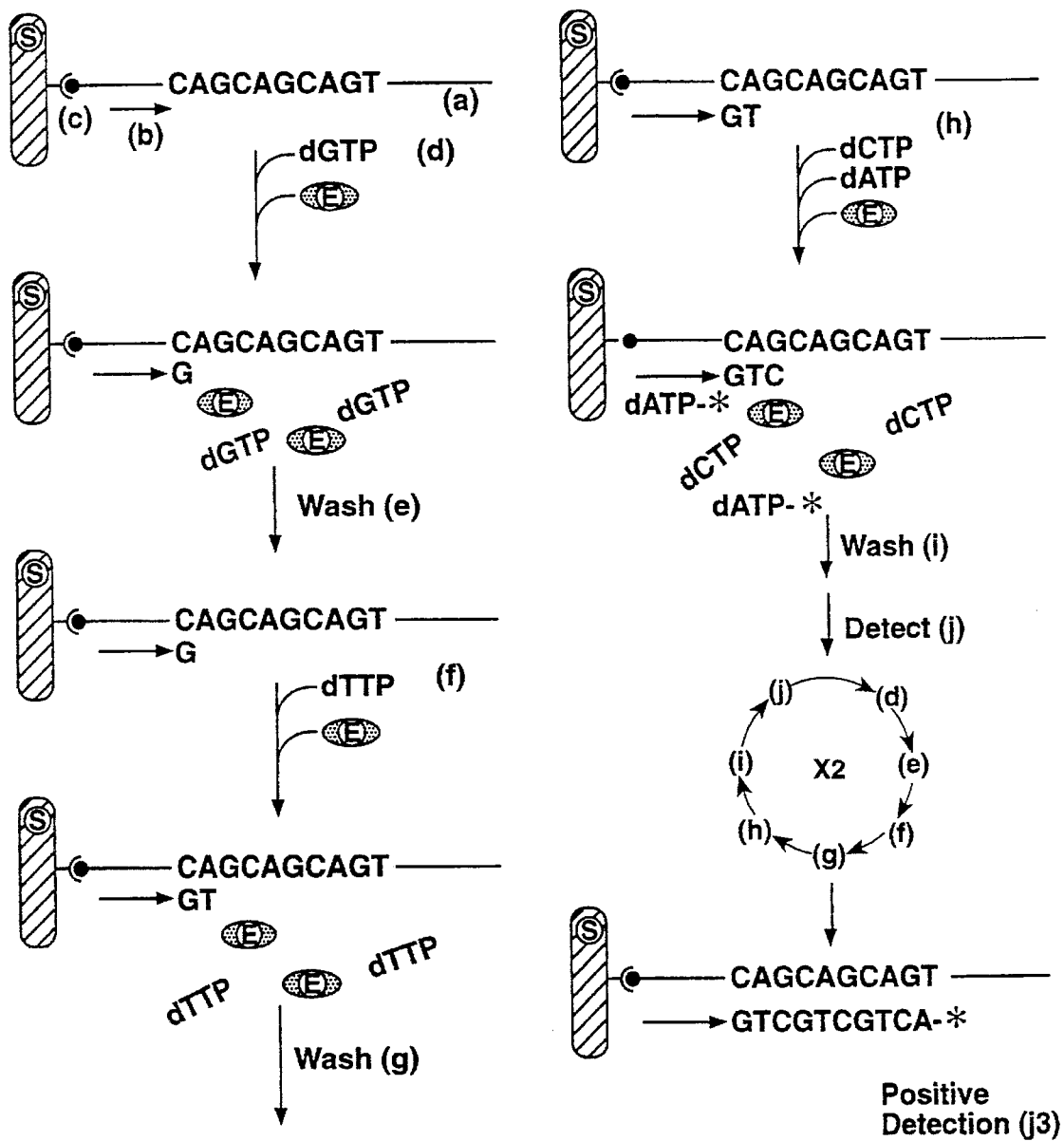
FIG. 1 is a schematic outline of features of a method aimed at quantifying the number of CAG trinucleotide repeats in examined nucleic acid sequence.

In order to better understand the embodiment of the present invention, reference is made to FIG. 1, which is a schematic depiction of a method aimed at quantifying the number of CAG trinucleotide repeats in examined nucleic acid sequence which includes: (a) if the nucleic acid of interest is not single stranded, treating the sample containing the nucleic acid to obtain unpaired nucleotide bases spanning the repeats and flanking regions; (b) under hybridization conditions, contacting the unpaired nucleotide bases with an oligonucleotide primer, having a sequence which is complementary to a stretch of nucleotide bases situated preferably 3' of the repeats region in the examined single strand sequence, preferably, the 3'-end of said oligonucleotide primer is annealed to the first nucleotide 3' of the repeats region; (c) providing means to ensure that at least the examined nucleic acid and the oligonucleotide primer are confined to a reaction chamber at all further steps; (d) the template primer hybrid is contacted with a primer extension unit which is capable of base pairing with the first nucleotide base in the core sequence of the repeats, dGTP in the given example, and a template dependent extension enzyme; (e) after a suitable incubation time, non-incorporated primer extension units are eliminated, preferably washed away; (f) the template primer hybrid, now said primer elongated by one unit, is contacted with a primer extension unit which is capable of base pairing with the second nucleotide base in the core sequence of the repeats, dTTP in the given example, and a template dependent extension enzyme; (g) after a suitable incubation time non-incorporated primer extension units are eliminated, preferably washed away; (h) the template primer hybrid, now said primer elongated by one additional unit, is contacted with a primer extension unit which is capable of base pairing with the third nucleotide base in the core sequence of the repeats, dCTP in the given example; a detection moiety containing, primer extension unit which is capable of base pairing with a nucleotide base 5' of the repeats region, said nucleotide base being the first nucleotide base of a type not included among the nucleotide bases in the core sequence of the trinucleotide repeats, dATP* in the given example; and a template dependent extension enzyme; (i) after a suitable incubation time non-incorporated primer extension units are eliminated preferably washed away; (j) detecting for the presence of the detection moiety containing primer extension unit; (k) steps (d) to (j) are repeated until detecting the detection moiety of the primer extension unit which is capable of base pairing with a nucleotide base 5' of the repeats region, said nucleotide base being the first nucleotide base of a type not included among the nucleotide bases in the core sequence of the trinucleotide repeats, dATP* in the given example; (l) the number of repeats as stated under (k) enables to calculate the number of trinucleotide repeats, CAG in the given example, therefore, enables the determination of the exact repetition number.

Figure 2:
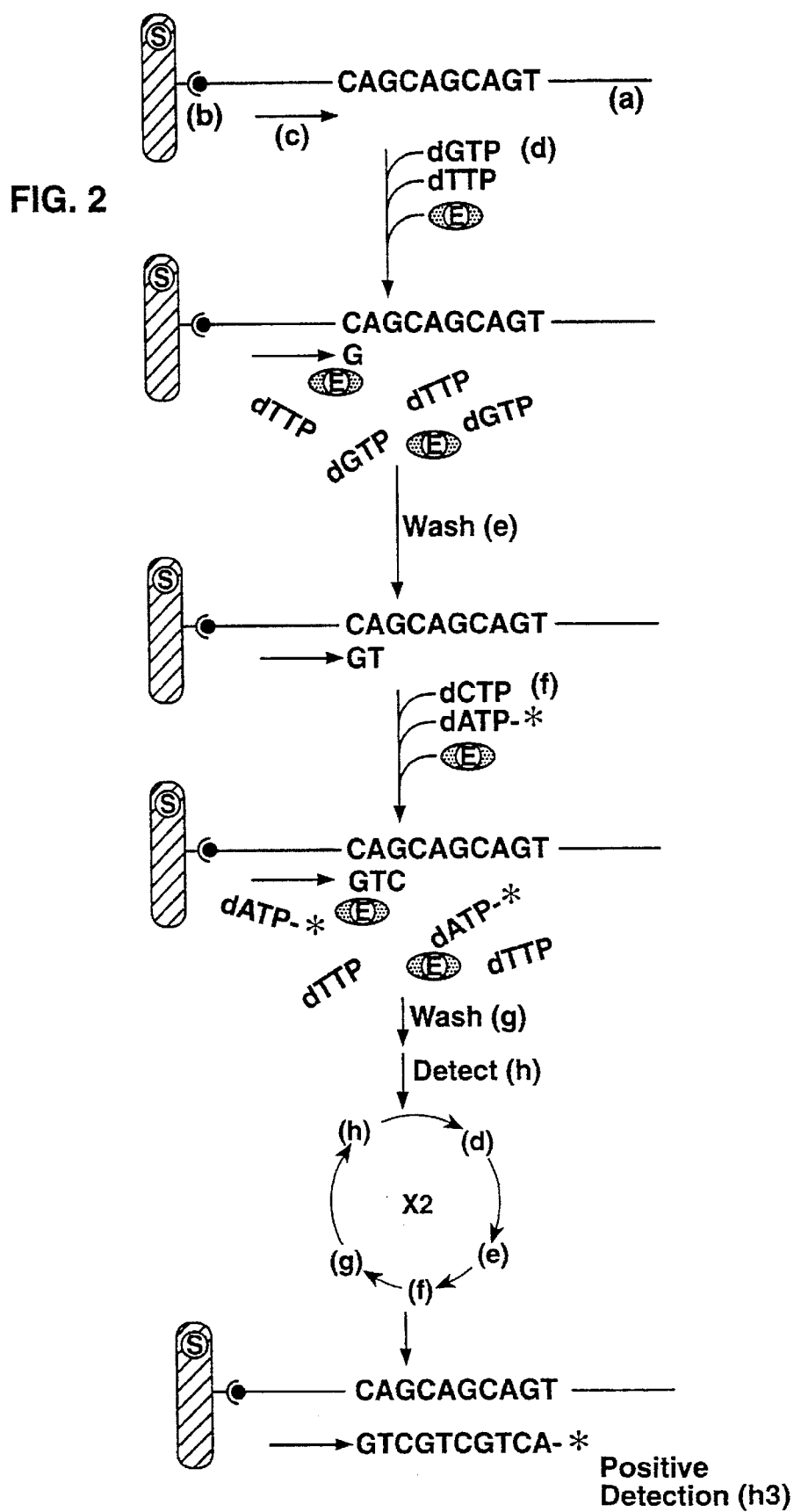
FIG. 2 is a schematic outline of features of modified and more efficient methods aimed at quantifying the number of CAG trinucleotide repeats in examined nucleic acid sequence.

In order to better understand the preferred embodiment of the present invention, reference is made to FIG. 2 which is a schematic depiction of modified and more efficient methods aimed at quantifying the number of CAG trinucleotide repeats in examined nucleic acid sequence which includes: (a) if the nucleic acid of interest is not already single stranded, treating a sample containing the nucleic acid to obtain unpaired nucleotide bases spanning the repeats and flanking regions; (b) under hybridization conditions, contacting the unpaired nucleotide bases with an oligonucleotide primer, having a sequence which is complementary to a stretch of nucleotide bases situated preferably 3' of the repeats region in the examined single strand nucleic acid template, preferably, the 3'-end of said oligonucleotide primer is annealed to the first nucleotide 3' of the repeats region; (c) providing means to ensure that the examined nucleic acid and the oligonucleotide primer are confined to a reaction chamber at all further steps; (d) the template primer hybrid is contacted with primer extension units which are capable of base pairing with the first and second nucleotide bases in the core sequence of the repeats, dGTP and dTTP in the given example, and a template dependent extension enzyme; alternatively (d') the template primer hybrid is contacted with a primer extension unit which is capable of base pairing with the first nucleotide bases in the core sequence of the repeats, dGTP in the given example, and a template dependent extension enzyme; (e) after a suitable incubation time non-incorporated primer extension units are eliminated, preferably washed away; (f) the template primer hybrid, now said primer elongated by two units, is contacted with a primer extension unit which is capable of base pairing with the third nucleotide base in the core sequence of the repeats, dCTP in the given example; a detection moiety containing, primer extension unit which is capable of base pairing with a nucleotide base 5' of the repeats region, said nucleotide base being the first nucleotide base of a type not included among the nucleotide bases in the core sequence of the trinucleotide repeats, dATP* in the given example; and a template dependent extension enzyme; alternatively (f) the template primer hybrid, now said primer elongated by one unit, is contacted with primer extension units which are capable of base pairing with the second and third nucleotide bases in the core sequence of the repeats, dTTP and dCTP in the given example; a detection moiety containing, primer extension unit which is capable of base pairing with a nucleotide base 5' of the repeats region, said nucleotide base being the first nucleotide base of a type not included among the nucleotide bases in the core sequence of the trinucleotide repeats, dATP* in the given example; and a template dependent extension enzyme; (g) after a suitable incubation time non-incorporated primer extension units are eliminated, preferably washed away; (h) detecting for the presence of the detection moiety containing primer extension unit; (i) steps (d) to (h) are repeated until detecting the detection moiety of the primer extension unit which is capable of base pairing with a nucleotide base 5' of the repeats region, said nucleotide base being the first nucleotide base of a type not included among the nucleotide bases in the core sequence of the trinucleotide repeats, dATP* in the given example; (j) the number of repeats as stated under (i) enables to calculate the number of trinucleotide repeats, CAG in the given example, therefore, enables the determination of the exact repetition number.

The human genome contains two alleles of each gene. Each of the alleles is located on one of the chromosomes making up a pair of homologue chromosomes. Alleles characterized by triple repeats are very polymorphic by nature, therefore most individuals contain non-identical alleles for each of their trinucleotide repeats containing genes, said alleles differ from one another by the number of trinucleotide repeats they contain. As explained, for diagnostic and prognostic purposes, it is important and crucial to determine the exact number of trinucleotide repeats contained in both alleles of the examined gene. In order to better understand the preferred embodiment of the present invention, reference is made to FIG. 3 which is a schematic depiction of a method aimed at simultaneous quantification of the number of a CAG trinucleotide repeats in two alleles each contains a different number of said repeats. According to this embodiment, steps of incorporating primer extension units complementary to the core sequence of the repeats are performed as detailed above until a detection of the detection moiety containing, primer extension unit which is capable of base pairing with a nucleotide base 5' of the repeats region, said nucleotide base being the first nucleotide base of a type not included among the nucleotide bases in the core sequence of the trinucleotide repeats, is made, and the magnitude of the signal recorded. Counting these steps enables to determine the number of trinucleotide repeats in the allele containing the lower number of repeats. After records have been made, steps of incorporating primer extension units complementary to the core sequence of the repeats are continued as detailed until further detection of the detection moiety containing, primer extension unit which is capable of base pairing with a nucleotide base 5' of the repeats region, said nucleotide base being the first nucleotide base of a type not included among the nucleotide bases in the core sequence of the trinucleotide repeats. Counting these steps and adding the resulted number to the former enables to determine the number of trinucleotide repeats in the allele containing the greater number of repeats.

Under this description, the detection moiety of the primer extension unit is non-removable, thus, as the second signal is obtained a summing of signals is made. Preferably a removable detection moiety may be used and removed after detecting the signal from the allele containing less repeats, alternatively, a different kind of detection moiety may be used, hence, the detection of the second signal is simpler since in both cases the second detection, as the first, is based on all or non-detection.

The embodiments of the present invention are also useful for determining the number of head to tail repeat sequences of two or more nucleotide bases, provided that the core sequence consists of no more than three types of nucleotide bases.

Methods according to preferred embodiments of the present invention enjoy a number of advantages relative to the prior art:

First, these are high resolution methods capable of a precise and unambiguous determination of the number of trinucleotide repeats in a selected locus contained in a genetic material sample and is therefore suitable for monitoring small variations in trinucleotide repeat numbers.

Second, the methods according to preferred embodiments of the present invention is capable of distinguishing between size variations due to trinucleotide repeats expansion/de-expansion or other molecular events such as the loss or formation of a restriction enzymes recognition site, such as the loss or gain of sequences due to deletions or insertions.

Third, these methods do not include any kind of gel electrophoresis or other size based separations and therefore may be easily automated diminishing the requirement for highly skilled personnel for their routine execution.

Fourth, ordinary personnel are sufficient for interpreting the results and for calculating the trinucleotide repeats number.

Finally, the high GC content of some of the trinucleotide repeats create gel migration artifacts due to the formation of strong secondary structures. Since the aforementioned methods of the invention aimed at the determination of trinucleotide repeats number are gel electrophoresis independent these artifacts, attributed to gel electrophoresis dependent methods, are circumvented.

The above described embodiments of the present invention may be made more efficient in term of costs by reusing materials, that is, after each step of the ones described, reagents are collected and are reused in further steps. A reconcentration and purification procedures may be needed before reuse of these reaction reagents is made.

The specific application of the inventive method for the quantification of trinucleotide repeats in genes known to carry such repeats is presently a preferred embodiment. In this application the method may be used as a diagnostic assay to determine the number of trinucleotide repeats present in individuals suffering from, or showing symptoms of, diseases known to be caused by expansion of such repeats in or close to specific genes. The method may also be applied for simultaneous screening of apparently healthy individuals to determine whether any of them are carriers of any such repeats. This is the case, for example, in the well elucidated Huntington's disease in which diseased individuals have expanded trinucleotide repeats in at least one allele encoding the IT15 gene. Furthermore, the method may also be applied for screening embryos by analyzing samples of amniotic fluid cells to determine whether the embryos have any known trinucleotide repeats expansion in one or two or none of the alleles encoding genes known to be involved in specific genetic diseases in which such expansions are involved.

The genetic material to be analyzed may, in principle, be any RNA or DNA obtained from the tissues or body fluids of humans, animals or plants or obtained from cultures of microorganisms or human, animal or plant cells or nucleic acid synthesized by extension enzyme. The genetic material may alternatively be obtained from non-living sources suspected of containing matter from living organism sources, as may be the case when applying the method in forensic medicine for detecting and identifying specific nucleotide sequences present in or on samples of clothing, furniture, weapons and other items found at the scene of a crime. In this instance, the genetic material obtained is usually in the form of DNA, since any RNA in such samples would normally have been degraded by ribonucleases.

The sample of nucleic acids can be dram from any source and may be natural or synthetic. The sample of nucleic acids may be made up of deoxyribonucleic acids, ribonucleic acids, or copolymers of deoxyribonucleic acid and ribonucleic acid. The nucleic acid of interest can be synthesized enzymatically in vitro, or synthesized non-enzymatically. The sample containing the nucleic acid or acids of interest can also comprise extragenomic DNA from an organism, RNA transcripts thereof, or cDNA prepared from RNA transcripts thereof. Also, the nucleic acid of interest can be synthesized by the polymerase chain reaction.

The examined nucleic acid can be made single stranded by using appropriate denaturing conditions, which may include heat, alkali, formamide, urea, glyoxal, enzymes, and combinations thereof.

Examination of nucleic acids obtained from two or more individuals can be made simultaneously, for initial screening purposes. Furthermore, some genes contain trinucleotide repeats which share identical repeat core sequence, nevertheless the trinucleotide repeats flanking regions differ substantially in their nucleotide base sequences. Therefore it is also possible to quantify the number of trinucleotide repeats in two or more genetic loci simultaneously.

The oligonucleotide primers can be any length or sequence, can be DNA or RNA, or any modification thereof. It is necessary, however, that the length and sequence of the oligonucleotide primers be chosen to optimize the specificity of the hybridization to the target sequences of interest.

Time and expense considerations tend to shift preference toward shorter oligonucleotides which are still sufficiently long to ensure high sequence specificity while at the same time ensuring rapid, easy and accurate preparation.

The oligonucleotide primer may be any suitable species, preferably an oligodeoxyribonucleotide, an oligoribonucleotide, a protein nucleic acid or a copolymer of deoxyribonucleotides, protein nucleic acids and ribonucleotides. The oligonucleotide primer can be either natural or synthetic. The oligonucleotide primer can be synthesized enzymatically in vivo, enzymatically in vitro, or non-enzymatically in vitro.

In addition, the oligonucleotide primer must be capable of hybridizing or annealing with a stretch of nucleotide bases present in the nucleic acid of interest preferably 3' of the trinucleotide repeats region to be quantified. One way to accomplish the desired hybridization is to have the template dependent primer be substantially complementary or fully complementary to the known nucleotide bases sequence preferably 3' of the trinucleotide repeats region to be quantified. For convenience, in some instances the 3'-end of the oligonucleotide primer may overlap part of the repeat sequences. Furthermore, the oligonucleotide primer may be suitable for annealing with any of the strands in the examined nucleic acid and the types of primer extension units used changed accordingly.

The single stranded examined nucleic acid and the oligonucleotide primer should be confined to a reaction chamber throughout the experimental steps in the method of the invention. This could be achieved, for example, by immobilizing any of the mentioned molecules to a solid support. The immobilization may be effected by binding the molecules to the solid support via (1) multiple ionic interactions between any of said molecules and the solid support; (2) multiple covalent bindings between the molecules and the solid support; (3) direct single point coupling of the molecules to the solid support (4) indirect single point coupling of the molecules to the solid support via an anchoring moiety conjugated to the molecules and a complement anchoring sites attached to the solid support, e.g., biotin conjugated to the single stranded examined nucleic acid or alternatively the oligonucleotide primer or both and avidin, streptavidin or antibiotin antibody are attached to the solid support; or magnetic beads are conjugated to the single stranded examined nucleic acid or alternatively the oligonucleotide primer or both and the solid support is a magnet or electromagnet. (5) indirect multiple points coupling of the molecules to the solid support via anchoring moieties conjugated to the molecules at multiple sites and a complement anchoring sites attached to the solid support. A single point coupling of the examined nucleic acid, or alternatively, the oligonucleotide primer or both to the solid support, whether direct as under (3); or indirect as under (4), is the preferred methodology since it maximizes the accessibility of other reaction components to these molecules and form less steric constrains.

In addition, the confinement of both the examined nucleic acid and the oligonucleotide primer to the reaction chamber may be effected by entrapping these molecules using a porous membrane with a molecular weight cut off that will facilitate the elimination of primer extension units via separative filtration and will, at the same time, retain the above mentioned molecules. While by immobilizing the mentioned molecules to a solid support the template dependent extension enzyme is discarded along with the primer extension units and therefore fresh enzyme should be added after each step, the enzyme, due to its high molecular weight, is retained upon entrapping the molecules using a porous membrane with a molecular weight cut off that will facilitate the elimination of primer extension units via separative filtration.

Any suitable extension moiety of the primer extension units may be used. The extension moiety however should contain a 3'-OH group enabling further elongation of the oligonucleotide primer. The extension moiety of the primer extension units may be deoxyribonucleotides, ribonucleotides or their 3'-OH containing analogs. Preferably, the extension moiety is a deoxyribonucleotide, such as dATP, dCTP, dGTP, dTTP and dUTP.

The elimination of non-incorporated primer extension units from the reaction chamber, preceding further incorporation steps as delineated above, may be effected via physically removing said primer extension units from the reaction chamber by, for example, filtration as mentioned, or alternatively, by destroying said primer extension units chemically or enzymatically within the reaction chamber, for example by alkaline phosphatase that will dephosphorilate said primer extension units, rendering them inapplicable for enzymatic incorporation.

Different versions of the methods for determining the number of trinucleotide repeats in a nucleic acid of interest are possible. In one version, the template is deoxyribonucleic acid, the primer is an oligodeoxyribonucleotide, oligoribonucleotide, protein nucleic acid, or a copolymer of deoxyribonucleotides, protein nucleic acids and ribonucleotides, and the template dependent enzyme is a DNA extension enzyme.

In a second version, the template is a ribonucleic acid, the primer is an oligodeoxyribonucleotide, oligoribonucleotide, protein nucleic acid or a copolymer of deoxyribonucleotides, protein nucleic acids and ribonucleotides, and the template dependent enzyme is a reverse transcriptase.

In a third version, the template is a deoxyribonucleic acid, the primer is an oligoribonucleotide, and the enzyme is an RNA extension enzyme.

In a fourth version, the template is a ribonucleic acid, the primer is an oligoribonucleotide, and the template dependent enzyme is an RNA replicase.

The template dependent enzyme preferably is confined to the reaction chamber. This could be achieved as described above by using a porous membrane with a molecular weight cut off that upon filtration will enable the elimination of primer extension units but will retain the enzyme. Alternatively, the enzyme may be linked via a long and flexible linking chain to a solid support, said solid support used also for immobilization of the examined nucleic acid and/or the oligonucleotide primer. The linking chain, being long and flexible, will allow the collision of the enzyme with its substrates, a prerequisite for catalysis. In both cases the addition of costly fresh enzyme in every incorporation step, as described above, is eliminated.

The nucleic acid of interest may contain non-natural nucleotide analogs such as deoxyinosine or 7 deaza 2' deoxyguanosine. These analogs destabilize DNA duplexes and could allow a primer annealing and extension reaction to occur in a double stranded sample without completely separating the strands.

Any suitable detection moiety of the primer extension unit which is capable of base pairing with a nucleotide base 5' of the repeats region, said nucleotide base being the first nucleotide base of a type not included among the nucleotide bases in the core sequence of the trinucleotide repeats, may be used. Furthermore, the detection moiety of the primer extension unit should have physical and chemical properties which do not interfere with its enzymatic addition to the 3'-OH group of the elongated oligonucleotide primer. The detection moiety of the primer extension unit may facilitate the direct or indirect detection of its presence. For indirect detection the detection moiety of the primer extension unit may include a molecule of a type selected from the group consisting of enzymes, catalysts, haptens, antibodies, substrates, coenzymes and chemiluminescence. Preferably the detection moiety of the primer extension unit facilitate the direct detection and may include a molecule of a type selected from the group consisting of fluorescence and radioactivity.

The detection moiety may be conjugated at any position to the primer extension unit. Furthermore, the detection moiety may be of a kind that is removable or destructible by chemical, physical or enzymatic manipulation. Removable or distractible detection moieties of the primer extension unit which is capable of base pairing with a nucleotide base 5' of the repeats region, said nucleotide base being the first nucleotide base of a type not included among the nucleotide bases in the core sequence of the trinucleotide repeats are preferably used, for reasons explained above, when the simultaneous quantification of two alleles each containing a different number of trinucleotide repeats is desired.

The detection of the detection moiety, to a very large extent, is dependent upon its chemical and physical properties. Any suitable detection approach may be selected. In a case where the detection moiety of the primer extension unit is non-removable, the detection, whether direct or indirect, is preferably carried out in the reaction camber. On the other hand, in a case where the detection moiety of the primer extension unit is removable, the detection, whether direct or indirect, may be carried out in a different chamber.

The ongoing research to determine the genetic basis for diseases and the advent of technologies such as the Polymerase Chain Reaction (PCR) has resulted in the discovery and complete sequencing of so far seven genes in which trinucleotide repeats expansion would lead to either no expression of the gene product or expression of a product which is qualitatively or quantitatively impaired and thereby resulting in a disease. Since trinucleotide repeats have been observed within or close to a number of human genes by gene bank searches, it is conceivable that trinucleotide amplification may be involved in the causation of other genetic diseases as well. There is thus an ever expanding field of application of the above method of the invention.

Since di- and trinucleotide repeats are highly polymorphic, that is for each gene characterized by such repeats at least few dozen alleles differing in their repeats number exist, the method of the invention may also be applied in the field of forensic medicine in which polymorphism in specific genes can be determined in, for example, blood or semen samples obtained at the scene of a crime and the results used to indicate whether or not a particular suspect was involved in the crime. Similarly, the aforesaid determination may also be used to determine whether a certain male individual is the father in cases of disputed paternity.

There is evidence that certain cancers may be the result of di- and trinucleotide-expansion in many gene targets, therefore, the present invention may be used as a cancer early diagnostic and prognostic tool.

Another application of the present methods is the detection of microorganisms in a sample on the basis of the presence of specific sequences in the sample. For example, an individual suspected of being infected by a microorganism, such as a bacteria or virus, can be tested by using an oligonucleotide primer which anneal only with a specific bacterial and/or viral DNA sequences and not with sequences present in the examined individual. The oligonucleotide primer's sequence is selected to enable its hybridization 3' of a stretch of nucleotide bases composed of one to three types of nucleotide bases followed by a different type of nucleotide base in the examined sequence and a procedure similar to the ones described above is carded out. Detecting the detection moiety of the primer extension unit that is complementary to said different type of nucleotide base is an indication of the presence of the examined genetic material in the sample. One example of such an application is in the screening of individuals for the presence of the AIDS virus.

The invention will now be further illustrated by the following examples:

EXAMPLES

Oligonucleotide primers and suitable detection moiety containing primer extension units aimed at the quantification of trinucleotide repeats in the seven genes known to carry said repeats As mentioned, so far seven genetic diseases each involving a unique genetic locus have been implicated with trinucleotide repeat mutations. These include: Fragile XA (A site, Martin Bell) syndrome (FRAXA); Kennedy disease (spinal and bulbar muscular atrophy, SBMA); Myotonic dystrophy (Curschmann Steinert, DM); Huntington's disease (HD); Spinocerebellar ataxia type 1 (SCA1); Fragile XE (E site) mental retardation (FRAXE MR); and Dentatorubral pallidoluysian atrophy (DRPLA).

Table I lists six of these diseases which are known to result from trinucleotide repeats expansion; appropriate 18 mer oligonucleotide primers, the upper primer being suitable for hybridization with a (−) strand therefore is suitable for hybridization with the (−) strand of single stranded DNA, whereas the lower primer being suitable for hybridization with a (+) strand therefore is suitable for hybridization with the (+) strand of single stranded DNA or enzymatically transcribed RNA; and detection moiety containing primer extension units suitable for determining the number of trinucleotide repeats as described above.

TABLE I

| Disease and (repeats core sequence): | Primers: | Extension units: |
|---|---|---|
| Fragile XA (CGG)n | 5' AGGGGGCGTGCGGCAGCG 3' (SEQ ID NO.: 1) | dT/ATP |
| | 5' CGGGCGCTCGAGGCCCAG 3' (SEQ ID NO.: 2) | dT/ATP |
| Kennedy disease (CAG)n | 5' GCCAGTTTGCTGCTGCTG 3' (SEQ ID NO.: 3) | dTTP |
| | 5' CCTGGGGCTAGTCTCTTG 3' (SEQ ID NO.: 4) | dATP |
| Myotonic dystrophy (GCT)n | 5' GTCCTTGTAGCCGGGAAT 3' (SEQ ID NO.: 5) | dATP |
| | 5' ATGGTCTCTCATCCCCCC3' (SEQ ID NO.: 6) | dTTP |
| Huntington's disease (CAG)n | 5' GAGTCCCTCAAGTCCTTC 3' (SEQ ID NO.: 7) | dTTP |
| | 5' CGGCGGTGGCGGCTGTTG3' (SEQ ID NO.: 8) | dATP |
| Spinocerebellar ataxia type 1 (CAG)n | 5' CCGGGACACAAGGCTGAG 3' (SEQ ID NO.: 9) | dTTP |
| | 5' CTGCTGCTGGATGCTGATG 3' (SEQ ID NO.: 10) | dATP |
| Dentatorubral pallidoluysian atrophy (CAG)n | 5' CACCACCAGCAACAGCAA 3' (SEQ ID NO.: 11) | dTTP |
| | 5' CCCAGAGTTTCCGTGATG 3' (SEQ ID NO.: 12) | dATP |

Methods aimed at the quantification of trinucleotide repeats

EXAMPLE 1

FIG. 1 illustrates a method aimed at quantifying the number of CAG trinucleotide repeats in examined nucleic acid sequence containing 3 said repeats followed by a thymine residue (—CAG CAG CAG T—). The sample containing the nucleic acid of interest is treated to obtain unpaired nucleotide bases spanning the repeats and fling regions (a). An oligonucleotide primer is annealed to the nucleic acid template under hybridization conditions, preferably the 3'-end of said oligonucleotide primer is annealed to the first nucleotide 3' of the repeats region (b). The examined nucleic acid is attached to a solid support (referred to as "S" in the Figure) indirectly via a single point coupling consisted of anchoring moiety conjugated to the molecules and a complement anchoring site attached to the solid support (c). The template primer hybrid is contacted with a dGTP primer extension unit which is capable of base pairing with the first nucleotide base in the core sequence of the repeats, and a template dependent extension enzyme, referred to as "E" in the Figure (d). After a suitable incubation time, non-incorporated dGTP primer extension unit is washed away along with the extension enzyme (e). The template primer hybrid, now said primer elongated by one guanine residue, is contacted with dTTP primer extension unit which is capable of base pairing with the second nucleotide base in the core sequence of the repeats, and a template dependent extension enzyme (f). After a suitable incubation time non-incorporated dTTP primer extension units are washed away (g). The template primer hybrid, now said primer elongated by guanine followed by thimine residues, is contacted with dCTP primer extension unit which is capable of base pairing with the third nucleotide base in the core sequence of the repeats, a dATP detection moiety containing, primer extension unit, referred to as "*" in the Figure, which is capable of base pairing with a nucleotide base 5' of the repeats region, said nucleotide base being the first nucleotide base of a type not included among the nucleotide bases in the core sequence of the trinucleotide repeats, and a template dependent extension enzyme (h). after a suitable incubation time, non-incorporated dCTP and dATP* primer extension units are washed away (i). Detecting for the presence of the detection moiety (*) containing dATP primer extension unit (j). Steps (d) to (j) are repeated altogether three times until detecting the detection moiety (*) of the dATP primer extension unit (j3). The number of repeats equals the number of the CAG trinucleotide repeats, therefore enabling determination of the exact repetition number.

EXAMPLE 2

FIG. 2 illustrates a modified and more efficient method aimed at quantifying the number of CAG trinucleotide repeats in examined nucleic acid sequence containing 3 said repeats followed by a thimine residue (—CAG CAG CAG T—). The sample containing the nucleic acid of interest is treated to obtain unpaired nucleotide bases spanning the repeats and flanking regions (a). An oligonucleotide primer is annealed to the nucleic acid template under hybridization conditions, preferably the 3'-end of said oligonucleotide primer is annealed to the first nucleotide 3' of the repeats region (b). The examined nucleic acid is attached to a solid support (S) indirectly via a single point coupling consisted of anchoring moiety conjugated to the molecules and a complement anchoring site attached to the solid support (c). The template primer hybrid is contacted with dGTP and dTTP primer extension units which are capable of base pairing with the first and second nucleotide bases in the core sequence of the repeats and a template dependent extension enzyme (E) (d). The template primer hybrid, now said primer elongated by a guanine and a thimine residues, is contacted with a dCTP primer extension unit which is capable of base pairing with the third nucleotide base in the core sequence of the repeats, a dATP detection moiety containing, primer extension unit (*) which is capable of base pairing with a nucleotide base 5' of the repeats region, said nucleotide base being the first nucleotide base of a type not included among the nucleotide bases in the core sequence of the trinucleotide repeats, and a template dependent extension enzyme (f). After a suitable incubation time non-incorporated dCTP and dATP* primer extension units are washed away (g). Detecting for the presence of the dATP* detection moiety containing, primer extension unit (h). Steps (d) to (h) are repeated altogether three times until detecting the detection moiety (*) of the dATP primer extension unit (h3). The number of repeats equals the number of the CAG trinucleotide repeats, therefore enabling determination of the exact repetition number.

EXAMPLE 3

Figure 3:
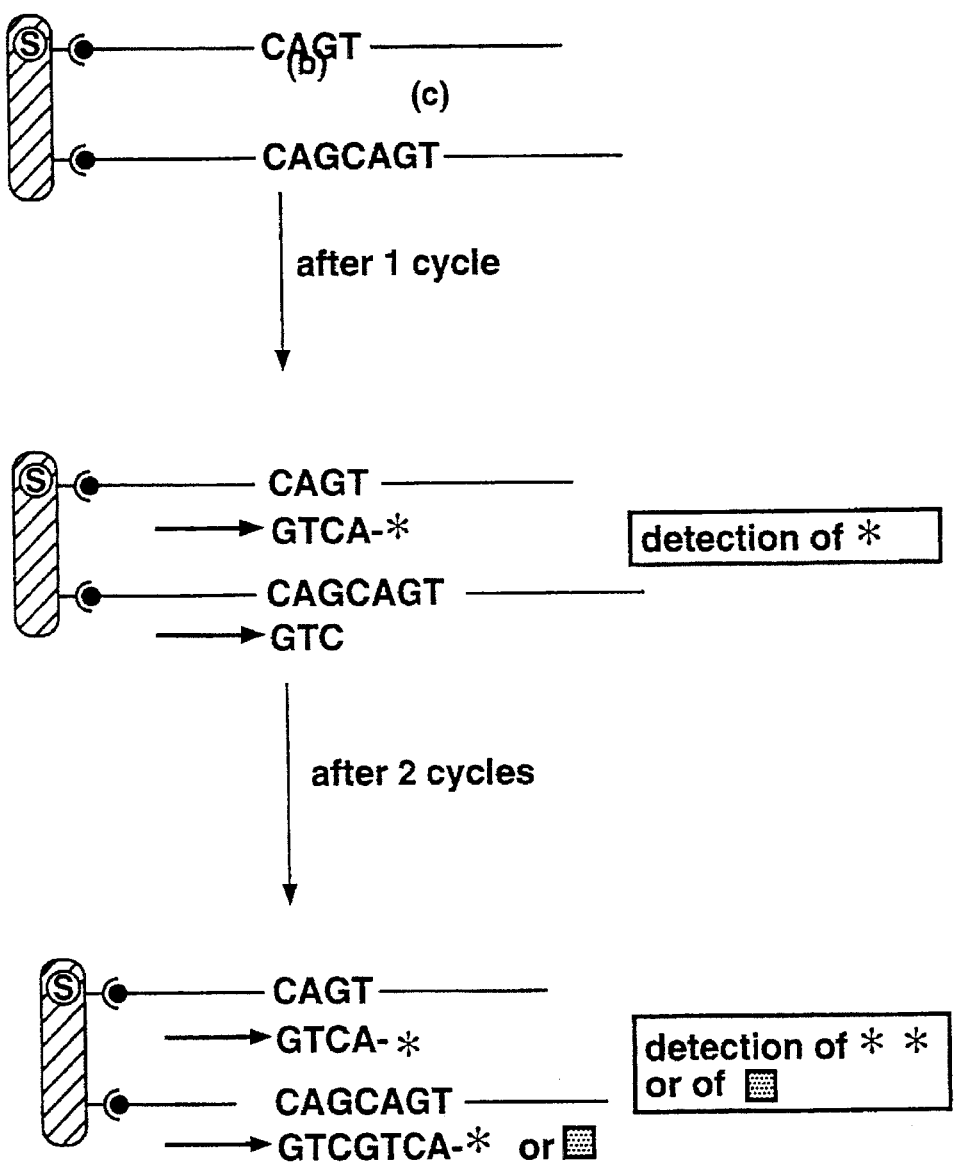
FIG. 3 is a schematic outline of features of a method aimed at simultaneous quantification of the number of CAG trinucleotide repeats in two alleles each contains a different number of said repeats.

FIG. 3 illustrates a method aimed at simultaneous quantification of the number of CAG trinucleotide repeats in two alleles the first containing one and the second two said repeats followed in both cases by a thimine residue. Steps of incorporating primer extension units complementary to the core sequence of the repeats are performed as detailed above until a detection of the detection moiety containing, primer extension unit (A*) which is capable of base pairing with a nucleotide base 5' of the repeats region, said nucleotide base being the first nucleotide base of a type not included among the nucleotide bases in the core sequence of the trinucleotide repeats, is made and the magnitude of the signal recorded (*). Counting these steps enables to determine the number of trinucleotide repeats in the allele containing the lower number of repeats. After records have been made, steps of incorporating primer extension units complementary to the core sequence of the repeats are continued as detailed until further detection of the detection moiety containing, primer extension unit (A*) which is capable of base pairing with a nucleotide base 5' of the repeats region, said nucleotide base being the first nucleotide base of a type not included among the nucleotide bases in the core sequence of the trinucleotide repeats is made and the magnitude of the additive signal (**) or a different signal, denoted as a closed box in the Figure, is recorded. Counting these steps (1 step in the given example) and adding the resulted number to the former (1 step in the given example) enables to determine the number of trinucleotide repeats in the allele containing the greater number of repeats (2 in the given example).

A diagnostic kit for quantifying trinucleotide repeat mutations

EXAMPLE 4

A diagnostic kit for carrying out a preferred embodiment of the methods according to the present invention detailed above may contain the following constituents:

a) any number of suitable oligonucleotide primers;

b) one to three primer extension units;

c) Further one or more primer extension units of a type not included under b), said primer extension units containing a detection moiety;

d) a suitable template dependent extension enzyme for carrying out the primer extension unit incorporation, or extension, steps of the method;

e) suitable buffer/s in aqueous solution for carrying out the annealing, extension, wash and detection steps of the method; and When the kit is to be used for Fragile XA; Kennedy disease; Myotonic dystrophy; Huntington's disease; Spinocerebellar ataxia type 1; Fragile XE mental retardation; and Dentatorubral pallidoluysian atrophy, it may contain, for example, any one or all of the specific oligonucleotide primers listed in Tables I above for quantifying the trinucleotide repeats expansions occurring in these genes. When the kit is to be used in the screening for the presence of one or all of the various listed genetic diseases, it may contain any suitable number of the oligonucleotide primers in any suitable combination. Different combinations of primers may be included in kits for different intended populations. When the kit is to be used forensic or paternity typing it may contain any combination of specific oligonucleotide primers, each designed to quantify a particular trinucleotide repeats contained in any of the mentioned or other genes. Depending on the circumstances, all of the kits may also contain any number of additional oligonucleotide primers suitable for determining the presence or absence of a DNA sequence corresponding specifically to the presence of a pathogen, for example, the presence of the AIDS virus. Accordingly, one kit may be used for testing any number of genes or gene, and this only requires that the kit contain a number of the specific oligonucleotide primers, all the other components of the kit being the same in all cases.

While the invention has been described with respect to a limited number of embodiments, it will be appreciated that many variations, modifications and other applications of the invention may be made.

An instrument for quantifying trinucleotide repeat mutations

EXAMPLE 5

Figure 4:
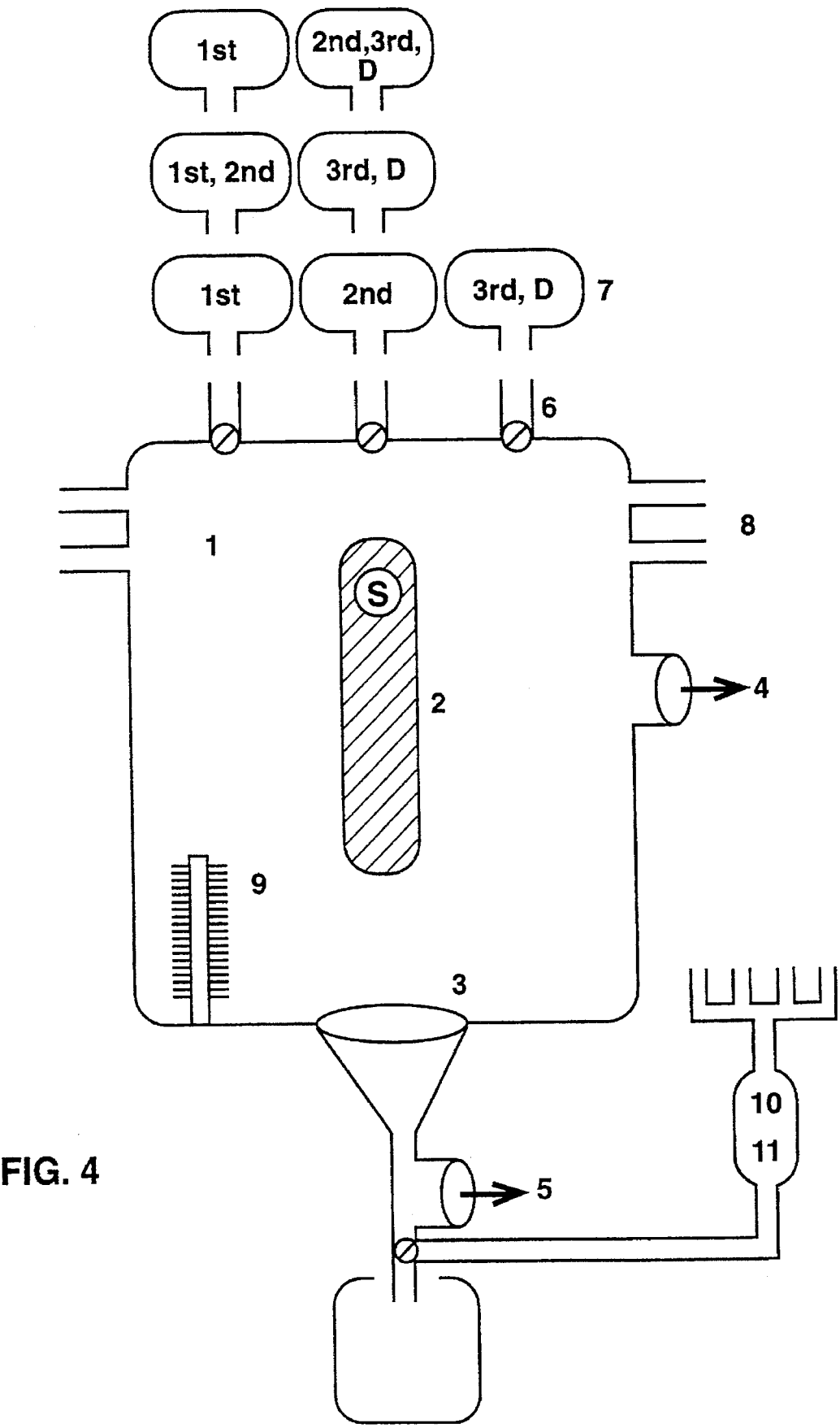
FIG. 4 is a schematic outline of features of an instrument suitable for executing the steps consisting the method of the invention.

FIG. 4 illustrates an automated instrument suitable for executing the steps in the method of the present invention for the determination of the number of trinucleotide repeats contained in specific genetic loci. The steps of the reaction are carried out in a reaction chamber (1) to which reagents may be added or eliminated via controllable valved tubing. Within the reaction chamber included is a solid support (2) suitable for immobilizing the nucleic acid of interest, the oligonucleotide primer or both. Alternatively or additionally the reaction chamber outlet contains a porous membrane (3) facilitating the retention of at least the nucleic acid of interest and the oligonucleotide primer while facilitating the separative filtration of primer extension units. Detector device (4) aimed at the detection of the detection moiety contained by the primer extension unit which is capable of base pairing with a nucleotide base 5' of the repeats region, said nucleotide base being the first nucleotide base of a type not included among the nucleotide bases in the core sequence of the trinucleotide repeats is located at the reaction chamber in cases where said detection moiety is of an non-removable type, alternatively, the detector device (5) may be located elsewhere, for example at the outlet, in cases where said detection moiety is of a removable type. The reaction chamber further contains two to three (6) inlets each connected to a reservoir (7) containing one to two types of the primer extension units capable of base pairing with the first (1st), second (2nd) and third (3rd) nucleotide base in the core sequence of the trinucleotide repeats. The second or third of said reservoir, depending upon the specific application, further contains a detection moiety containing, primer extension unit (D) which is capable of base pairing with a nucleotide base 5' of the repeats region, said nucleotide base being the first nucleotide base of a type not included among the nucleotide bases in the core sequence of the trinucleotide repeats. Further reservoirs and inlets for the administration of materials such as a suitable template dependent enzyme; reaction buffer, wash buffer/s, detection buffer/s (sensitizer) and the like materials may also be included (8). The reaction chamber and any reversoire may be temperature controlled (9). Tubing connecting the reaction chamber outlet with any of the reservoirs may be added as well as a reconcentration (10) and/or purification (11) device aimed at the reuse of discarded materials. The instrument may be operated manually or preferably automatically for example the instrument operation may be controlled by a built in or external computer.

What is claimed is:

1. A method of quantifying the number of trinucleotide repeats in a nucleic acid of interest, comprising the steps of:

(a) if the nucleic acid of interest is double stranded, treating the nucleic acid of interest to obtain unpaired nucleotide bases spanning the trinucleotide repeats and their flanking regions, or, if the nucleic acid of interest is single stranded, directly employing step (b);

(b) contacting the unpaired nucleotide bases spanning the number of trinucleotide repeats and their flanking regions with an oligonucleotide primer for hybridizing with a stretch of nucleotide bases present in the nucleic acid of interest partially or fully 3' of the nucleotide repeats to be quantified, so as to form a duplex between the primer and the nucleic acid of interest;

(c) providing means for confining the nucleic acid of interest and the oligonucleotide primer to a reaction chamber at all further steps (d) through (k); and further comprising the cycled steps of:

(d) contacting the template primer duplex with a first primer extension unit for base pairing with one of the nucleotide bases, in the core sequence of the trinucleotide repeats, and with a template dependent extension enzyme;

(e) eliminating non-incorporated units of said first primer extension units;

(f) contacting the template primer duplex, which primer is now extended by one unit as described in step (d), with a second primer extension unit for base pairing with a second nucleotide base, in the core sequence of the repeat, said second nucleotide base being located adjacent to and immediately 5' of the nucleotide base employed under step (d), and with a template dependent extension enzyme;

(g) eliminating non-incorporated units of said second primer extension units;

(h) contacting the template primer duplex, which primer is now elongated by one further additional unit as described in step (f), with:

(i) a third primer extension unit for base pairing with a third nucleotide base, in the core sequence of the repeat, said third nucleotide base being located adjacent to and immediately 5' of the nucleotide base under step (f);

(ii) a detection moiety which is conjugated with a fourth primer extension unit for base pairing with a nucleotide base 5' of the repeats, said nucleotide base being the first nucleotide base of a type not included among the nucleotide bases in the core sequence of the trinucleotide repeats, said detection moiety which is conjugated with said fourth primer extension unit may be present in selected cycles of this stage; and (iii) a template dependent extension enzyme;

(i) eliminating non-incorporated units of said third and fourth primer extension units;

(j) if step (h) included said detection moiety which is conjugated with said fourth primer extension unit, detecting the presence of said detection moiety; and if no detection is obtained, (k) repeating steps (d) to (j) until said detection moiety is detected, said detection of said detection moiety being indicative of the number of trinucleotide repeats included in the nucleic acid of interest.

2. A method as in claim 1, wherein the nucleic acid of interest is selected from the group consisting of synthetic and natural deoxyribonucleic acid, ribonucleic acid, and a copolymer of deoxyribonucleic acid and ribonucleic acid.

3. A method as in claim 1 wherein the oligonucleotide primer is selected from the group consisting of oligodeoxyribonucleotides, oligoribonucleotides, protein nucleic acids and copolymers of oligodeoxyribonucleotides, protein nucleic acids and oligoribonucleotides.

4. A method as in claim 1, wherein the oligonucleotide primer is substantially complementary to said stretch of nucleotide bases present in the nucleic acid of interest partially or fully 3' of the nucleotide repeats to be quantified.

5. A method as in claim 1, wherein the oligonucleotide primer is fully complementary to said stretch of nucleotide bases present in the nucleic acid of interest partially or fully 3' of the nucleotide repeats to be quantified.

6. A method as in claim 1, wherein the confining of the nucleic acid and the oligonucleotide primer to a reaction chamber at all steps is effected by a process selected from the group of techniques consisting of direct and indirect-, single and multiple-immobilization to a solid support, combinations thereof and molecular weight cut off filtration.

7. A method as in claim 1, wherein the extension moiety of said first, second and third primer extension unit is selected from the group consisting of deoxyribonucleotides, ribonucleotides and their 3'-OH containing analogs, and said fourth primer extension unit is selected from the group consisting of deoxyribonucleotides, ribonucleotides, dideoxynucleotides and their analogs.

8. A method as in claim 1, wherein the extension moiety of said first, second and third primer extension units is selected from the group consisting of dATP, dCTP, dGTP, dTTP, dUTP, ATP, CTP, GTP, TTP and their 3'-OH containing analogs and the extension moiety of said fourth primer extension units is selected from the group consisting of dATP, dCTP, dGTP, dTTP, dUTP, ATP, CTP, GTP, TTP, ddATP, ddCTP, ddGTP, ddTTP and their analogs.

9. A method as in claim 1, wherein the elimination of the primer extension units is effected by a process selected from the group of techniques consisting of washing, filtering and chemical, enzymatic and physical destruction.

10. A method as in claim 1, wherein the detection moiety of the primer extension unit is situated at any position on said primer extension unit and is selected from the group of types consisting of direct and indirect detection moieties.

11. A method as in claim 1, wherein the detection moiety of the primer extension unit is selected from the group of types consisting of removable, non-removable and destructible chemical groups.

12. A method as in claim 1, wherein steps (d) and (f) and steps (e) and (g) are combined under two successive single steps, in the first combined single step said template-primer duplex is contacted with the first and second primer extension units for base pairing with two adjacent nucleotide bases in the core sequence of the repeats, and a template dependent extension enzyme, while in the second combined single step said non-incorporated first and second primer extension units are eliminated.

13. A method as in claim 12, wherein the nucleic acid of interest is selected from the group consisting of synthetic and natural deoxyribonucleic acid, ribonucleic acid, and a copolymer of deoxyribonucleic acid and ribonucleic acid.

14. A method as in claim 12 wherein the oligonucleotide primer is selected from the group consisting of oligodeoxyribonucleotides, oligoribonucleotides, protein nucleic acids and copolymers of oligodeoxyribonucleotides, protein nucleic acids and oligoribonucleotides.

15. A method as in claim 12, wherein the oligonucleotide primer is substantially complementary to said stretch of nucleotide bases present in the nucleic acid of interest partially or fully 3' of the nucleotide repeats to be quantified.

16. A method as in claim 12, wherein the oligonucleotide primer is fully complementary to said stretch of nucleotide bases present in the nucleic acid of interest partially or fully 3' of the nucleotide repeats to be quantified.

17. A method as in claim 12, wherein the confining of the nucleic acid and the oligonucleotide primer to a reaction chamber at all steps is effected by a process selected from the group of techniques consisting of direct and indirect-, single and multiple-immobilization to a solid support, combinations thereof and molecular weight cut off filtration.

18. A method as in claim 12, wherein the extension moiety of said first second and third primer extension unit is selected from the group consisting of deoxyribonucleotides, ribonucleotides and their 3'-OH containing analogs, and said fourth primer extension unit is selected from the group consisting of deoxyribonucleotides, ribonucleotides, dideoxynucleotides and their analogs.

19. A method as in claim 12, wherein the extension moiety of said first second and third primer extension units is selected from the group consisting of dATP, dCTP, dGTP, dTTP, dUTP, ATP, CTP, GTP, TTP and their 3'-OH containing analogs and the extension moiety of said fourth primer extension units is selected from the group consisting of dATP, dCTP, dGTP, dTTP, dUTP, ATP, CTP, GTP, TTP, ddATP, ddCTP, ddGTP, ddTTP and their analogs.

20. A method as in claim 12, wherein the elimination of the primer extension units is effected by a process selected from the group of techniques consisting of washing, filtering and chemical, enzymatic and physical destruction.

21. A method as in claim 12, wherein the detection moiety of the primer extension unit is situated at any position on said primer extension unit and is selected from the group of types consisting of direct and indirect detection moieties.

22. A method as in claim 12, wherein the detection moiety of the primer extension unit is selected from the group of types consisting of removable, non-removable and destructible chemical groups.

23. A method as in claim 1, wherein steps (f) and (h) and steps (g) and (i) are combined under two single steps, in the first combined single step said template-primer duplex, now said primer extended by one unit, is contacted with:

(i) said second and third primer extension units for base pairing with two adjacent nucleotide bases in the core sequence of the repeats;

(ii) a detection moiety which is conjugated with said fourth primer extension unit, said detection moiety which is conjugated with said fourth primer extension unit may be present in selected said cycles of this stage; and (iii) a template dependent extension enzyme;

while in the second combined single step, said non-incorporated second third and fourth primer extension units are eliminated.

24. A method as in claim 23, wherein the nucleic acid of interest is selected from the group consisting of synthetic and natural deoxyribonucleic acid, ribonucleic acid, and a copolymer of deoxyribonucleic acid and ribonucleic acid.

25. A method as in claim 23 wherein the oligonucleotide primer is selected from the group consisting of oligodeoxyribonucleotides, oligoribonucleotides, protein nucleic acids and copolymers of oligodeoxyribonucleotides, protein nucleic acids and oligoribonucleotides.

26. A method as in claim 12, wherein the oligonucleotide primer is fully complementary to said stretch of nucleotide based present in the nucleic acid of interest partially or fully 3' of the nucleotide repeats to be quantified.

27. A method as in claim 23, wherein the oligonucleotide primer is fully complementary to said stretch of nucleotide bases present in the nucleic acid of interest partially or fully 3' of the nucleotide repeats to be quantified.

28. A method as in claim 23, wherein the confining of the nucleic acid and the oligonucleotide primer to a reaction chamber at all steps is effected by a process selected from the group of techniques consisting of direct and indirect-, single and multiple- immobilization to a solid support, combinations thereof and molecular weight cut off filtration.

29. A method as in claim 23, wherein the extension moiety of said first, second and third primer extension unit is selected from the group consisting of deoxyribonucleotides, ribonucleotides and their 3'-OH containing analogs, and said fourth primer extension unit is selected from the group consisting of deoxyribonucleotides, ribonucleotides, dideoxynucleotides and their analogs.

30. A method as in claim 23, wherein the extension moiety of said first, second and third primer extension units is selected from the group consisting of dATP, dCTP, dGTP, dTTP, dUTP, ATP, CTP, GTP, TTP and their 3'-OH containing analogs and the extension moiety of said fourth primer extension units is selected from the group consisting of dATP, dCTP, dGTP, dTTP, dUTP, ATP, CTP, GTP, TTP, ddATP, ddCTP, ddGTP, ddTTP and their analogs.

31. A method as in claim 23, wherein the elimination of the primer extension units is effected by a process selected from the group of techniques consisting of washing, filtering and chemical, enzymatic and physical destruction.

32. A method as in claim 23, wherein the detection moiety of the primer extension unit is situated at any position on said primer extension unit and is selected from the group of types consisting of direct and indirect detection moieties.

33. A method as in claim 23, wherein the detection moiety of the primer extension unit is selected from the group of types consisting of removable, non-removable and destructible chemical groups.

34. A method of quantifying the number of dinucleotide repeats in a nucleic acid of interest, comprising the steps of:
(a) if the nucleic acid of interest is double stranded, treating the nucleic acid of interest to obtain unpaired nucleotide bases spanning the dinucleotide repeats and their flanking regions, or, if the nucleic acid of interest is single stranded, directly employing step (b);
(b) contacting the unpaired nucleotide bases spanning the number of dinucleotide repeats and their flanking regions with an oligonucleotide primer for hybridizing with a stretch of nucleotide bases present in the nucleic acid of interest partially or fully 3' of the nucleotide repeats to be quantified, so as to form a duplex between the primer and the nucleic acid of interest;
(c) providing means for confining the nucleic acid of interest and the oligonucleotide primer to a reaction chamber at all further steps (d)–(i); and
further comprising the cycled steps of:
(d) contacting the template primer duplex with a first primer extension unit for base pairing with one of the nucleotide bases, in the core sequence of the dinucleotide repeats, and with a template dependent extension enzyme;
(e) eliminating non-incorporated units of said first primer extension units;
(f) contacting the template primer duplex, which primer is now extended by one unit as described in step (d), with:
(i) a second primer extension unit for base pairing with a second nucleotide base, in the core sequence of the repeat, said second nucleotide base being located adjacent to and immediately 5' of the nucleotide base under step (d);
(ii) a detection moiety which is conjugated with a third primer extension unit for base pairing with a nucleotide base 5' of the repeats, said nucleotide base being the first nucleotide base of a type not included among the nucleotide bases in the core sequence of the dinucleotide repeats, said detection moiety which is conjugated with said third primer extension unit may be present in selected cycles of this stage; and
(iii) a template dependent extension enzyme;
(g) eliminating non-incorporated units of said second and third primer extension units;
(h) if step (f) included said detection moiety which is conjugated with said third primer extension unit, detecting the presence of said detection moiety; and if no detection is obtained,
(i) repeating steps (d) to (h) until said detection moiety is detected, said detection of said detection moiety being indicative of the number of dinucleotide repeats included in the nucleic acid of interest.

35. A method aimed at simultaneous quantification of the number of nucleotide repeats having a core sequence which includes two or three nucleotides, in two alleles, each of said alleles containing any number of said repeats wherein steps of incorporating primer extension units complementary to the core sequence of the repeats are performed as derailed under claim 1, 12, 23 or 34 until a detection of said detection moiety incorporated onto said primer annealed to a nucleic acid associated with the allele containing a lower number of repeats is made, and steps of incorporating primer extension units complementary to the core sequence of the repeats are continued until a further detection of a detection moiety incorporated onto said primer annealed to the nucleic acid associated with the allele containing a higher number of repeats is made.

36. A method as in claim 35, wherein the nucleic acid of interest is selected from the group consisting of synthetic and natural deoxyribonucleic acid, ribonucleic acid, and a copolymer of deoxyribonucleic acid and ribonucleic acid.

37. A method as in claim 35 wherein the oligonucleotide primer is selected from the group consisting of oligodeoxyribonucleotides, oligoribonucleotides, protein nucleic acids and copolymers of oligodeoxyribonucleotides, protein nucleic acids and oligoribonucleotides.

38. A method as in claim 35, wherein the oligonucleotide primer is substantially complementary to said stretch of nucleotide bases present in the nucleic acid of interest partially or fully 3' of the nucleotide repeats to be quantified.

39. A method as in claim 35, wherein the oligonucleotide primer is fully complementary to said stretch of nucleotide bases present in the nucleic acid of interest partially 3' of the nucleotide repeats to be quantified.

40. A method as in claim 35, wherein the confining of the nucleic acid and the oligonucleotide primer to a reaction chamber at all steps is effected by a process selected from the group of techniques consisting of direct and indirect-, single and multiple- immobilization to a solid support, combinations thereof and molecular weight cut off filtration.

41. A method as in claim 35, wherein the extension moiety of said first, second and third primer extension unit is selected from the group consisting of deoxyribonucleotides, ribonucleotides and their 3'-OH containing analogs, and said fourth primer extension unit is selected from the group consisting of deoxyribonucleotides, ribonucleotides, dideoxynucleotides and their analogs.

42. A method as in claim 35, wherein the extension moiety of said first, second and third primer extension units is selected from the group consisting of dATP, dCTP, dGTP, dTTP, dUTP, ATP, CTP, GTP, TTP and their 3'-OH containing analogs and the extension moiety of said fourth primer extension units is selected from the group consisting of dATP, dCTP, dGTP, dTTP, dUTP, ATP, CTP, GTP, TTP, ddATP, ddCTP, ddGTP, ddTTP and their analogs.

43. A method as in claim 35, wherein the elimination of the primer extension units is effected by a process selected from the group of techniques consisting of washing, filtering and chemical, enzymatic and physical destruction.

44. A method as in claim 35, wherein the detection moiety of the primer extension unit is situated at any position on said primer extension unit and is selected from the group of types consisting of direct and indirect detection moieties.

45. A method as in claim 35, wherein the detection moiety of the primer extension unit is selected from the group of types consisting of removable, non-removable and destructible chemical groups.

* * * * *

SEQUENCE LISTING ( 1 ) GENERAL INFORMATION:

( i i i ) NUMBER OF SEQUENCES:12

( 2 ) INFORMATION FOR SEQ ID NO:1:

( i ) SEQUENCE CHARACTERISTICS:
        ( A ) LENGTH:18
        ( B ) TYPE:nucleic acid
        ( C ) STRANDEDNESS:single
        ( D ) TOPOLOGY:linear ( x i ) SEQUENCE DESCRIPTION: SEQ ID NO:1:

AGGGGGCGTG CGGCAGCG      18

( 2 ) INFORMATION FOR SEQ ID NO:2:

( i ) SEQUENCE CHARACTERISTICS:
        ( A ) LENGTH:18
        ( B ) TYPE:nucleic acid
        ( C ) STRANDEDNESS:single
        ( D ) TOPOLOGY:linear ( x i ) SEQUENCE DESCRIPTION: SEQ ID NO:2:

CGGGCGCTCG AGGCCCAG      18

( 2 ) INFORMATION FOR SEQ ID NO:3:

( i ) SEQUENCE CHARACTERISTICS:
        ( A ) LENGTH:18
        ( B ) TYPE:nucleic acid
        ( C ) STRANDEDNESS:single (D) TOPOLOGY:linear (xi) SEQUENCE DESCRIPTION: SEQ ID NO:3:

GCCAGTTTGC TGCTGCTG     18

(2) INFORMATION FOR SEQ ID NO:4:

(i) SEQUENCE CHARACTERISTICS:
       (A) LENGTH:18
       (B) TYPE:nucleic acid
       (C) STRANDEDNESS:single
       (D) TOPOLOGY:linear (xi) SEQUENCE DESCRIPTION: SEQ ID NO:4:

CCTGGGGCTA GTCTCTTG     18

(2) INFORMATION FOR SEQ ID NO:5:

(i) SEQUENCE CHARACTERISTICS:
       (A) LENGTH:18
       (B) TYPE:nucleic acid
       (C) STRANDEDNESS:single
       (D) TOPOLOGY:linear (xi) SEQUENCE DESCRIPTION: SEQ ID NO:5:

GTCCTTGTAG CCGGGAAT     18

(2) INFORMATION FOR SEQ ID NO:6:

(i) SEQUENCE CHARACTERISTICS:
       (A) LENGTH:18
       (B) TYPE:nucleic acid
       (C) STRANDEDNESS:single
       (D) TOPOLOGY:linear (xi) SEQUENCE DESCRIPTION: SEQ ID NO:6:

ATGGTCTCTC ATCCCCCC     18

(2) INFORMATION FOR SEQ ID NO:7:

(i) SEQUENCE CHARACTERISTICS:
       (A) LENGTH:18
       (B) TYPE:nucleic acid
       (C) STRANDEDNESS:single
       (D) TOPOLOGY:linear (xi) SEQUENCE DESCRIPTION: SEQ ID NO:7:

GAGTCCCTCA AGTCCTTC     18

(2) INFORMATION FOR SEQ ID NO:8:

(i) SEQUENCE CHARACTERISTICS:
       (A) LENGTH:18
       (B) TYPE:nucleic acid
       (C) STRANDEDNESS:single
       (D) TOPOLOGY:linear (xi) SEQUENCE DESCRIPTION: SEQ ID NO:8:

CGGCGGTGGC GGCTGTTG     18

(2) INFORMATION FOR SEQ ID NO:9:

(i) SEQUENCE CHARACTERISTICS:
       (A) LENGTH:18
       (B) TYPE:nucleic acid
       (C) STRANDEDNESS:single
       (D) TOPOLOGY:linear ( x i ) SEQUENCE DESCRIPTION: SEQ ID NO:9:

CCGGGACACA AGGCTGAG       18

( 2 ) INFORMATION FOR SEQ ID NO:10:

( i ) SEQUENCE CHARACTERISTICS:
        ( A ) LENGTH:19
        ( B ) TYPE:nucleic acid
        ( C ) STRANDEDNESS:single
        ( D ) TOPOLOGY:linear ( x i ) SEQUENCE DESCRIPTION: SEQ ID NO:10:

CTGCTGCTGG ATGCTGATG      19

( 2 ) INFORMATION FOR SEQ ID NO:11:

( i ) SEQUENCE CHARACTERISTICS:
        ( A ) LENGTH:18
        ( B ) TYPE:nucleic acid
        ( C ) STRANDEDNESS:single
        ( D ) TOPOLOGY:linear ( x i ) SEQUENCE DESCRIPTION: SEQ ID NO:11:

CACCACCAGC AACAGCAA       18

( 2 ) INFORMATION FOR SEQ ID NO:12:

( i ) SEQUENCE CHARACTERISTICS:
        ( A ) LENGTH:18
        ( B ) TYPE:nucleic acid
        ( C ) STRANDEDNESS:single
        ( D ) TOPOLOGY:linear ( x i ) SEQUENCE DESCRIPTION: SEQ ID NO:12:

CCCAGAGTTT CCGTGATG       18